United States Patent
Roschin et al.

(10) Patent No.: US 8,952,074 B2
(45) Date of Patent: *Feb. 10, 2015

(54) MEDICINAL AGENT FOR TREATING PATIENTS SUFFERING FROM DISEASES CAUSED BY THE MONOAMINOOXIDASE EXCESSIVE ACTIVITY AND A METHOD FOR TREATING PATIENTS SUFFERING FROM DISEASES CAUSED BY THE MONOAMINOOXIDASE EXCESSIVE ACTIVITY

(76) Inventors: Viktor Ivanovich Roschin, St. Petersburg (RU); Vagif Sultanovich Sultanov, St. Petersburg (RU)

(*) Notice: Subject to any disclaimer, the term of this patent is extended or adjusted under 35 U.S.C. 154(b) by 593 days.

This patent is subject to a terminal disclaimer.

(21) Appl. No.: 12/601,405

(22) PCT Filed: May 14, 2008

(86) PCT No.: PCT/RU2008/000299
§ 371 (c)(1),
(2), (4) Date: Feb. 22, 2010

(87) PCT Pub. No.: WO2008/143553
PCT Pub. Date: Nov. 27, 2008

(65) Prior Publication Data
US 2010/0172963 A1 Jul. 8, 2010

(30) Foreign Application Priority Data
May 23, 2007 (RU) .............................. 2007119233

(51) Int. Cl.
| | | |
|---|---|---|
| *A61K 9/127* | (2006.01) | |
| *A61K 31/045* | (2006.01) | |
| *A61P 9/12* | (2006.01) | |
| *A61P 25/24* | (2006.01) | |
| *A61P 25/08* | (2006.01) | |
| *C07C 33/03* | (2006.01) | |
| *A61K 9/48* | (2006.01) | |
| *A61K 31/08* | (2006.01) | |
| *A61K 31/20* | (2006.01) | |
| *A61K 31/765* | (2006.01) | |

(52) U.S. Cl.
CPC . *A61K 9/48* (2013.01); *A61K 9/127* (2013.01); *A61K 31/045* (2013.01); *A61K 31/08* (2013.01); *A61K 31/20* (2013.01); *A61K 31/765* (2013.01)
USPC ......... 514/739; 424/450; 424/474; 568/909.5

(58) Field of Classification Search
None
See application file for complete search history.

(56) References Cited

FOREIGN PATENT DOCUMENTS

| GB | 2310138 A | * | 8/1997 |
| RU | 2137479 C1 | * | 9/1999 |
| RU | 2252026 C1 | | 5/2005 |

OTHER PUBLICATIONS

Solagran Company announcement, Sep. 20, 2005.*
Human translation of Russian Patent RU 2137479 C1.*
V. L. Sviderskii, et al. A Comparative Study of the Effect of the Polyprenol Preparation Ropren from Coniferous Plants on the Key Enzymes of the Cholinergic and Monoaminergic Types of Nervous Transmission. Doklady Biochemistry and Biophysics, 2006, vol. 408, pp. 148-151. Cover Date is Jun. 1, 2006.*
Hammen, C. Stress and Depression. Annu. Rev. Clin. Psychol. 2005. 1:293-319. First published online as a Review in Advance on Oct. 11, 2004.*
J. C. Shih, K. Chen, and M. J. Ridd. Monoamine Oxidase: From Genes to Behavior. Annu. Rev. Neurosci. 1999. 22:197-217.*
Solagran Limited Company Announcement Final Results of Bloeffective R Alzheimer's Disease Trial. Dated Sep. 20, 2005. Downloaded from the Australian Securities Exchange Website on Feb. 19, 2014: http://www.asx.com.au/asxpdf/20050920/pdf/3sd7g0mczqbnc.pdf.*
Solagran Limited, "Company Announcement Final Results of Bioeffective R Alzheimer's Disease Trail", Sep. 20, 2005, pp. 1-6, Found from the Internet URL:hhtp://wrww.osullivanpllc.com/news/050920 solagran.pdf.

* cited by examiner

*Primary Examiner* — Frederick Krass
*Assistant Examiner* — Michael P Cohen
(74) *Attorney, Agent, or Firm* — Foley & Lardner LLP

(57) ABSTRACT

The invention relates to the chemical and pharmaceutical industry and to medicine, in particular, to medicinal agents based on a mixture of natural oligomers of isoprenol (Ropren), which inhibits monoamine oxidase (MAO) activity; and to a method for treatment of patients suffering from diseases associated with the excessive activity of monoamine oxidase.
The given invention consists of the development of a new therapeutic substance with minimal side effects that is currently a topical issue for treatment of the corresponding diseases.
The proposed:
  Therapeutic substance consisted of polyprenols of formula (1) for treatment of patients with diseases associated with excessive activity of monoamine oxidase.

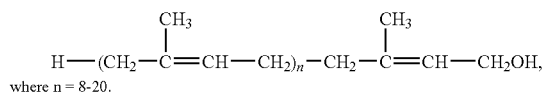

where n = 8-20.

with content of polyprenols of formula (1) in the given therapeutic substance from 0.1 to 80%.
  The treatment method of diseases associated with excessive activity of monoamine oxidase, which consists of administration to the patients of a single or multiple doses of polyprenols of formula (1) in the amount of 1 to 150 mg per day, in the form of an individual agent or as a pharmaceutical composition including excipients.

12 Claims, No Drawings

MEDICINAL AGENT FOR TREATING PATIENTS SUFFERING FROM DISEASES CAUSED BY THE MONOAMINOOXIDASE EXCESSIVE ACTIVITY AND A METHOD FOR TREATING PATIENTS SUFFERING FROM DISEASES CAUSED BY THE MONOAMINOOXIDASE EXCESSIVE ACTIVITY

TECHNOLOGICAL FIELD

The invention relates to the chemical and pharmaceutical industry and to medicine, in particular, to medicinal agents based on a mixture of natural oligomers of isoprenol (Ropren), which inhibits monoamine oxidase (MAO) activity and to a method for treatment of patients suffering from diseases associated with the excessive activity of monoamine oxidase.

LEVEL OF TECHNOLOGICAL INVENTION

Therapeutic agents with selective ability to inhibit monoamine oxidase A or monoamine oxidase B are widely used in medicine for treatment of depressive conditions, panic attacks, phobia, anxiety, migraine, and imbecility, including senile dementia. The efficacy of inhibitors of monoamine oxidase (MAO) has been established in case of prophylaxis, treatment or relief of conditions of patients suffering from neurodegenerative diseases, for instance Alzheimer's, Parkinson, or Huntington diseases, and the related symptoms of the above-mentioned diseases that progress the reduction of cognitive functions (Veselovskiy A. V., Biomedicine Chemistry 2004 vol. 50 ed. 3 p. 314-321; patent RU 2141482; U.S. Pat. Nos. 5,792,799; 2,017,607; Uoyudim M. D. et al Mech. Ageing Dev. 2005 February; 126(2): 317-26; Weinstock M et al. Prog. Neuropsychopharmacol. Biol. Psychiatry. 2003 Jun. 27(4):555-61; Carreiras M C, Marco J L. Curr. Pharm. Des. 2004; 10(25):3167-75; WO 2004/089351; WO 2005/079756; US 2005176777).

The application of MAO inhibitors for treatment of dependency from psychoactive therapeutic agents, smoking, and for suppressing withdrawal syndromes has been established (US 2002/0128299; WO 95/28934; WO 96/35425).

Such broad application of MAO inhibitors can be explained by the significant role of monoamine oxidase in the regulation of monoamine-neurotransmitters, serotonin and dopamine (Castagnoli N., Dalvie D. et al. Chem.-Res.-Toxicol. 2001 14:1139-1162). This flavoprotein catalyses oxidation of different exogenous amines, preferably monoamines in the central nervous system (CNS) and peripheral tissues. Its catalytic activity changes in many pathological conditions. In view of the important physiological role of amines in cellular apoptosis, growth, and proliferation, MAO is a target of research into pharmacological agents in neuropathology Inhibition of MAO-A facilitates accumulation of monoamines and by preventing normal termination of their mediator activity, leads to an amplification of the sympathoadrenal system. Reyes, Marc G et al. presume that degeneration of neurons and possibly degeneration of the synaptic transmission in the substantia nigra relates to a reduction of metabolism of dopamine (Neurol. Res. Mar. 2003; 25: 179-182).

Classic MAO inhibitors are amines that have a substitution in the α-position. They often have affinity to MAO and inhibit the enzyme without being deaminated. Such amines include indopan, α-methylmethylbenzilamine, as well as tertiary amines, which can form dystopic complexes with MAO that prevent deamination of MAO.

Other inhibitors of MAO are inhibitors of the hydrazide structure, for instance, iprazide, which slows deamination of tyramine. It has been established that the antidepressant activity of such inhibitors is accompanied by an increased content of monoamines in the central nervous system. It is assumed that the activity of MAO inhibitors can include bonding of a metal or flavine cofactor in the active centre.

However, a change in MAO activity can happen not only under effect of direct inhibitors, but also under effect of some substances, such as estradiol, hydrogen peroxide or copper ions. MAO gains the ability to deaminate various nitrogen-containing substances, many of which are substrates of diamine oxidases—histamine, spermine, etc. Such change in enzymatic activity is called transformation, unlike inhibition, where catalytic properties do not change.

The closest analogue of the claimed invention is Gliatilin (therapeutic agent based on choline alfoscerate, which contain 40.5% of choline), which is a therapeutic substance with the selective ability to inhibit MAO (application EP1203584). However, the effect of treatment with Gliatilin was registered mainly in patients with vascular brain deficiency (patent RU 2217143) and alcohol encephalopathy. Improvement of cognitive functions was registered only in patients with a weak or moderate level of dementia, however, in case of moderately-severe course of dementia the effect of the substance was not identified (Odinak M. M., Voznyuk I. A. New approaches in therapy of acute or chronic pathology of the nervous system, Manual, SPb, HMA, 2001, p. 62).

NOVELTY OF INVENTION

The objectives of the invention include the development of a new therapeutic agent and a method for treatment of diseases associated with excessive activity of MAO, which would be free from the above-mentioned disadvantages; as well as a search for new therapeutic agents with minimal side effects, which currently remains a topical issue in the treatment of different neurodegenerative diseases.

The authors suggested that polyprenols of the following formula (1)

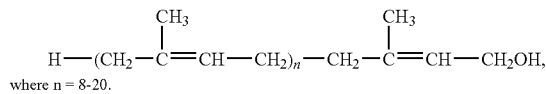

where n = 8-20.

represent a therapeutic substance, which can affect MAO activity, normalising it by means of membrane-tropic activity. In formula (1), n is 8-20, and can preferably be 10-16 (n=10-16).

Polyprenols of formula (1) (compounds of formula (1)) can be used as a therapeutic substance for the treatment of diseases caused by excessive activity of monoamine oxidase, with content of the above-mentioned polyprenols in the given therapeutic substance ranging from 0.1 to 80%. The treatment method for diseases caused by excessive activity of monoamine oxidase consists of administration to the patients of one or several doses of polyprenols of formula (1) of 1 to 150 mg per day, in the form of the individual substance or as a pharmaceutical composition including excipients.

The compounds of formula (1) (Ropren) is of interest as an enhancer of common antidepressants, due to its unique membrane-active properties.

As noted above, MAO is a mitochondrial enzyme, strongly connected with lipoprotein membrane of mitochondria.

According to data in the literature, aliphatic alcohols with long hydrocarbon chains can affect the activity of MAO. Based on the comparison of these factors and the experimental results obtained, it can be assumed that Ropren, which is an isoprenol alcohol containing isoprenoid links and active α-tails of these links, can restore MAO activity to normal levels. Ropren can have the following mechanism of action: as a lipophilic substance Ropren dissolves in lipids, interacts with components of mitochondrial membranes, thus increasing their permeability or the availability for corresponding substrates for allowing enzymatic activity of MAO. The increased permeability of the membrane can lead to changes in the process of deamination. As demonstrated above, many psychiatric disorders are related to increased MAO activity. Therefore, it seems appropriate to search for compounds with low toxicity, especially of natural origin, for prophylaxis and treatment of such psychiatric disorders as manic-depressive conditions, schizophrenia, and suicidal syndrome.

Since the noradrenergic system has an inhibiting effect on the GABA-ergic system of the brain (the principal inhibiting system of CNS), an increase in activity of the noradrenergic system leads to disinhibition and intensification of stimulation processes in the CNS.

It is known that in patients with various psychiatric disorders, including Alzheimer's and Parkinson disease, MAO activity in the blood plasma is always increased.

EXAMPLES OF THE PREFERRED EXECUTION OF INVENTION

For the first time, the authors demonstrated the capacity of the mixture of polyprenols with general formula (1) (called Ropren) to inhibit and/or normalise the level of monoamine oxidase.

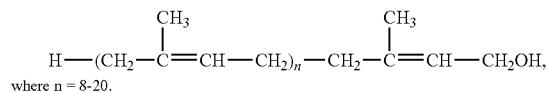

where n = 8-20.

This natural mix of oligomers (isoprenols) acts as one substance, but can be divided into individual isoprenols using reverse phase sorbents.

Ropren can be derived from green coniferous species (patent RU2017782). This polyprenol has demonstrated an anti-ulcerous effect (N. A. Skuya et al. Products of processing of green verdure—perspective of using in gastroenterology: Functional diagnostics and efficacy of treatment of diseases of digestive apparatus Vilnius 1988 part 4 pg. 675-676), hepatoprotector (U.S. Pat. No. 5,731,357), anti-tumour activity and efficacy in prevention of metastases after surgical removal of tumours (Kuznescov S. et al., Carotenoids and polyprenols: molecular mechanisms of their interaction and potential for use in oncology. In edition: Carotenoids in Oncology, M., 1992, pp. 84-88).

It is preferable to obtain a more pure fraction of isoprenols, Ropren, by a method, described in patent RU2238291. This method is based on the extraction of green conifer needles and foliage of deciduous species using an organic solvent, with subsequent isolation by settling during cooling, and filtering of waxes; separation of free acids from the obtained solution of extractive compounds in hydrocarbon solvent with alkali solution; fractionalisation of the obtained neutralised solution of salts of solution of neutral compounds in hydrocarbon solvent and a water-alkaline solution of salts of organic acids, distillation of solvents from neutral compounds, and isolation of neutral compounds. The neutral substances are subsequently extracted with acetone and $C_1$-$C_3$ alcohol. Mass ratio of neutral compounds to acetone is from 1:2 to 1:5. A part of neutral substances made up of concentrates of higher fatty acid esters with triterpene alcohol, stearins, higher fatty alcohol precipitates, and the acetone-soluble residue contains acetates of polyprenols. By treating the residue with alcohol after distillation of acetone, the total diterpene alcohols are separated from polyprenols acetates, which are insoluble in alcohol. Saponification of the polyprenol acetates with alcoholic alkali solution results in obtaining polyprenols concentrate. These polyprenols have a density of 0.893-0.897 g/ml and are obtained by chromatography of the given concentrate using silica gel with a ratio of substance:sorbent of 1:10 in hexane, or in hexane with addition of 5% and 10% of diethyl ether with sorbent-solvent ratio of 1:1. The HPLC chromatogram should contain peaks with a shape and location typical for chromatograms of polyprenols of formula (1). Chromatography set-up: 3.0×150 mm column filled with extracting agent octadecyl silica gel of X-Terra $C_{18}$ type or similar; mobile phase—acetone-methanol mixture (80:20); flow rate—1 ml/min.

With fatty degeneration of the liver not related to alcoholism, MAO activity in the human liver increases on average by 40%. A similar phenomenon takes place in the livers of mice with congenital obesity and hyperglycemia. It is known, that hepatotoxins such as $CCl_4$ (carbon tetrachloride) and allyl formate have a damaging effect on MAO in the liver of rabbits. It is known that changes in MAO activity in the rat liver also occurs during hepatocarcinogenesis induced by administration of 2-acetylaminofluorene and diethylnitrosamine. It has been demonstrated, that some pharmaceuticals based on natural compounds have the capacity to positively affect MAO activity in cases of liver cirrhosis.

The effect of Ropren on the increased MAO activity in acute experimental conditions (the effect of carbon tetrachloride administration) was studied at the Sechenov I. M. at the Institute of Evolutionary Physiology and Biochemistry, St-Petersburg, Russia. Rats, weighing 180-200 g and kept at conditions determined by the international standards, were divided into 3 groups of 21 rats.

$1^{st}$ group: Control group 1—intact animals. On $7^{th}$, $14^{th}$, and $21^{st}$ day, animals were euthanized and their liver and brain extracted for analysis.

$2^{nd}$ group: Control group 2—animals had 50% increase of MAO activity in the liver mitochondria, experimentally induced by subcutaneous administration of carbon tetrachloride. On $7^{th}$, $14^{th}$, and $21^{st}$ day, animals were euthanized and their liver and brain extracted for analysis.

$3^{rd}$, group: Experimental group—animals also received carbon tetrachloride via subcutaneous administration. Ropren in a form of oil solution was administered with meat mince at the dose of 60 mg/kg, starting from the $2^{nd}$ day and to the end of the experiment. On $7^{th}$, $14^{th}$, and $21^{st}$ day, animals were euthanized and their liver and brain extracted for analysis.

Immediately after preparation, organs were frozen and kept at −5° C. Organs were homogenised and partially cleaned from ballast substances by extraction in 0.0075 M potassium phosphate buffer pH 7.4, using the method of Severina I. S. (Biochemistry 1979 44(2): 195-204). Mitochondria were isolated from a 10% homogenate in 0.25 M saccharose by centrifuging at 13,000 g (this step occurs after removal of nuclei and cell fragments by centrifuging of homogenate for 3 minutes at 600 g). The obtained fraction was once again precipitated using the same conditions, suspended in 0.0075 M potassium-phosphate buffer pH 7.4 (20-25 mg of protein per ml), and stored at −20° C. In order to obtain the fragments of mitochondrial membranes, the suspension was thawed, suspended in a 10-fold volume of the same buffer, centrifuged in cold conditions at 20,000 g, supernatant liquid removed, and the deposit (with fragments of mitochondrial membranes) was suspended in the same buffer. The MAO preparations obtained by the cited above method were frozen and stored for 2-3 days until the beginning of analysis.

Protein content in enzyme preparations was measured as per Lowry. MAO activity was determined using the spectrophotometric method (wavelength of 420 nm) by measuring amount of ammonia formed over 60 minutes as a result of the enzymatic oxidative deamination of monoamine tyramine-hydrochloride (Sigma, USA). Samples (final volume of 2.5 ml) contained fragments of mitochondrial membranes in the amount corresponding to 3 mg protein; substrate 2 mM of tyramine or 5 mM of serotonin, and 0.0075 M of phosphate buffer, pH 7.4. Samples were incubated for 60 minutes at 37° C. in an $O_2$ environment. One ml of 50% trichloracetic acid was added, and protein residue was removed by centrifuging at 7,500 g for 5 minutes. The amount of ammonia freed during the monoamine oxidase reaction was measured in the protein-free filtrate, as per the modified Convey method with subsequent Nesslerisation (Severina I. S., Biochemistry 1979 44 (2): pp. 195-204; Strelkov R. B., Laboratory work, 1967, No. 1, pp. 17-19). The results obtained were statistically processed using Student's t-test. It was demonstrated that during all experiments, MAO activity in the rat liver in the Control group 2 was higher than in the Control group 1 (intact animals) by 50%. In the experimental group, by the 7th day Ropren reduced the increased MAO activity (not significant) in comparison with control 2. However, by the $14^{th}$ and $21^{st}$ day of the experiment, the MAO activity was reduced (by 17-23%) to the level in control 1 (statistically significant reduction) (Table 1).

of developing hepatic encephalopathy. A different degree of MAO inhibition was established in various sections of the brain: 53% on average in hypothalamus, 68.5% in medulla, and 70% in striatum. By the $21^{st}$ day, in experimental group, Ropren and Gliatilin restored MAO function on average by 66-70% in comparison to the intact rats and by 28-32% in comparison to the affected rats. In the control group, by the $21^{st}$ day, MAO activity remained reduced in all sections of the brain as the result of the exposure to carbon tetrachloride, with subsequent suppression of MAO activity; no restoration of MAO function occurred throughout the entire experiment. Ropren, just like Gliatilin, restored functional activity of MAO. The effect of Ropren is considered to be related to the participation of this drug in repair processes of damaged membranes, or in processes of enzyme transformation caused by changes in the viscosity of the lipid bilayer of mitochondrial membranes in the brain. The data obtained indicate the reparative and restoring effect of the compounds of formula (1).

MAO activity in patients with clinical conditions was determined spectrophotometrically (at 241 nm) based on the amount of benzaldehyde that forms as a result of the enzymatic reaction of oxidative deamination of monoamines in the blood plasma (Zeinalov T. A., Gorkin V. Z. Issues of medical chemistry, 1990, 36 (1): 78-81). The blood plasma of 20 patients before and after treatment with Ropren was obtained by the traditional method of processing venous blood. It was stored until the analysis at −20° C. Samples (final volume of 1.5 ml) contained 0.25 ml of the blood plasma, 0.15 ml of 10 mM of substrate of benzilamine and 1.1 ml of 0.04 M of phosphate buffer, pH 7.4. The samples were incubated for 180 min at 37.0 C.°. The reaction was stopped by adding 0.2 ml of 1 M HCl.

The normal value of MAO activity in healthy individuals (blood donors) is on average 0.44 nmol per 1 ml of plasma per 1 min. MAO activity in the examined patients varied (depending on their age and condition) from 0.57-1.26 nmol per 1 ml

TABLE 1

MAO activity in rat liver (in nmol of released ammonia per minute per mg of protein) on $7^{th}$, $14^{th}$, and $21^{st}$ day of experiment

| Group of animals (21 rats in each group) | $7^{th}$ day | | | $14^{th}$ day | | | $21^{st}$ day | | |
|---|---|---|---|---|---|---|---|---|---|
| | MAO activity in liver | % to $1^{st}$ control | % to $2^{nd}$ control | MAO activity in liver | % to $1^{st}$ control | % to $2^{nd}$ control | MAO activity in liver | % to $1^{st}$ control | % to $2^{nd}$ control |
| $1^{st}$ control (intact) | 2.26 ± 0.16 | 100 | — | 2.31 ± 0.18 | 100 | — | 2.40 ± 0.17 | 100 | — |
| $2^{nd}$ control (exposed to $CCl_4$ (0.2 ml/100 g)) | 3.37 ± 0.14 | 149* | 100 | 3.51 ± 0.14 | 152* | 100 | 3.53 ± 0.17 | 147* | 100 |
| $CCl_4$ (0.2 ml/100 g) + Ropren (60 mg/kg) | 3.15 ± 0.12 | 139* | 93 | 2.91 ± 0.13 | 126* | 83* | 2.73 ± 0.18 | 114* | 77* |

In another experiment, researchers studied three sections of the brain (hypothalamus, medulla, and striatum) in animals after treatment with Ropren and Gliatilin. Use of Ropren led to restoration of the altered MAO activity in the animals, caused by carbon tetrachloride. Gliatilin, a source of phospholipids and choline, was used as a comparator drug. Study of the effect of carbon tetrachloride on the activity of the membrane-binding enzyme MAO in all sections of the brain demonstrated inhibition of MAO activity throughout the entire experiment. Use of $CCl_4$ leads to disruption of neurotransmission and functioning of all mediator systems that are connected to the damage of the liver mitochondria in cases of plasma per 1 min before treatment (except for 3 patients −0.19-0.28 nmol per 1 ml of plasma per 1 min). After completion of treatment with Ropren, MAO activity decreased by between 0.47 to 0.91 nmol per 1 ml of plasma per 1 min. (Table 2 and 3). Comparison of results of the blood test of each patient before and after the treatment showed the following: MAO activity of blood plasma in the patients was higher than normal before the treatment (by 1.3-2.9 times) and only in 3 patients was it lower than normal and did not change after the treatment (data obtained from the patients was not included for referencing range of parameters of MAO activity after the treatment). As a result of the treatment, MAO activity decreased in almost all patients to normal or close to normal values (i.e. by 1.5-3 times). Therefore, it was demonstrated that Ropren has an inhibiting effect on MAO activity in the blood plasma (Table 2 and 3).

For administration to patients, Ropren can be used as a part of pharmaceutical composition in combination with one or more pharmaceutically acceptable carriers, solvents and excipients.

Examples of pharmaceutical compositions include any solid (such as tablets, pills, capsules, granules, etc.) or liquid (such as solutions, suspensions, emulsions) therapeutic forms for internal administration, traditional forms for parenteral administration, or in a form of rectal suppositories or aerosols.

Compositions for oral administration can contain traditional excipients. They can be in solid or liquid forms: tablets, capsules, solutions, suspensions or syrups; and they can contain any acceptable excipients such as binding agents (e.g. sugar, gelatine, sorbitol, tragacanth, polyvinylpyrrolidone), diluents/fillers (eg lactose, sugar, starch, calcium phosphate, sorbitol), tablet lubricants (e.g. magnesium stearate), disintegrants (e.g. starch, polyvinylpyrrolidone, microcrystalline cellulose, carboxymethyl cellulose), wetting agents (e.g. sodium lauryl sulphate), dispersing or surface-active substances. Liquid forms for oral administration can include solvents (water, vegetable or animal oils, or mineral oil), dextrose and other solutions of saccharides, glycols. The mentioned compositions are prepared using conventional methods.

Composition for parenteral administration can be prepared by both traditional pharmaceutical methods (solutions, suspensions), and in a form of water micro-emulsions, as per patent RU 2189231, based on Hanks solution with 10% of ethanol. They can include water, pharmaceutically acceptable fats or oils, alcohols or other organic solvents, surfactants and/or antioxidants, and/or preservatives.

Normal concentrations of the compound of formula (1) are within the range from 0.1% to 80%. Finished compositions can contain a single dose or be produced in a form of ampoules or vials, which contain several single doses. If necessary, finished therapeutic forms can contain stabilizers, buffer systems, and other excipients.

Agents for rectal administration can include traditional substances for this form, such as paraffin, vegetable, animal or mineral fats or oils, emulsifiers, polyethylene glycol, lauryl sulphate or sulphate salts, mineral acids or sodium hydrogen carbonate.

The effective amount, as per the claimed use, is within the range from 1 to 150 mg and can be administered in the form of single or several doses per day. More specific doses depend on type of pathology, patient's condition, presence of accompanying diseases, as selection of doses and duration of treatment are strictly individualised.

The efficacy of the treatment with polyprenols of formula (1) of depressive conditions in cases of various neurodegenerative disorders and/or dependence from psychoactive substances, nicotine, ethanol, and/or withdrawal symptoms from psychoactive substances, nicotine, or ethanol was demonstrated in the examples cited below.

Clinical trials of Ropren were conducted at the Scvortsov-Stepanov Municipal Psychiatric Hospital No 3 (Saint-Petersburg).

The efficacy of the treatment of patients with various types of dementia, including Alzheimer's disease and with Parkinson's syndrome, was evaluated based on the MAO activity in the blood serum, and on changes in cognitive functions before and after the treatment, using the international scale MMSE, unified scale for evaluation of Parkinsonism, EEG data, and biochemical blood indices.

In patients with dementia of various geneses, the blood was sampled from a vein for determination of MAO activity, during 3 months of treatment in the hospital: before, during, and at the end of the treatment.

The initial MAO activity in the blood plasma of these patients varied. Therefore, we divided them into two groups depending on the severity of the disease. The first group included the patients with a moderate-severe form of dementia and with initially increased parameters of MAO activity in the blood plasma (13 people).

This group was mainly comprised of the patients over 60 and 76 y.o., with a history of the disease from 6 months to 4 years. The patients had marked dementia and psychotic symptoms and severe chronic diseases in anamnesis ($2^{nd}$ degree diabetes, coronary heart disease, hypertension, hepatitis B or C).

The inhibiting effect of Ropren on MAO in the first group of patients with age dementia and background of organic or vascular brain disorders, and cranio-cerebral traumas is presented in Table 2.

TABLE 2

Inhibiting effect of Ropren and changes of enzymatic activity of MAO in blood plasma of patients

| | | | Parameters | | MAO activity (nmol of released ammonia per minute per mg of protein) | | |
|---|---|---|---|---|---|---|---|
| No | No. of patient's card | Age | History of disease | Evaluation of mental status before and after treatment (points) | Before treatment | After 2 months | After treatment |
| 1 | 1 | 63 | 3 months | 10/5 | 0.63 | 0.48 | 0.47 |
| 2 | 2 | 74 | 1 year | 20/21 | 0.86 | 0.59 | 0.57 |
| 3 | 3 | 74 | 1 year | 16/18 | 0.57 | 0.46 | 0.49 |
| 4 | 4 | 71 | 1 year | 20/24 | 0.97 | — | 0.71 |
| 5 | 5 | 63 | 1.5 years | 24/26 | 1.09 | 0.50 | 0.48 |
| 6 | 6 | 67 | 2 years | 26/26 | 0.64 | — | 0.56 |
| 7 | 7 | 62 | 6 months | 24/28 | 0.63 | 0.45 | 0.43 |
| 8 | 8 | 66 | 6 months | 21/27 | 1.22 | — | 0.83 |
| 9 | 12 | 68 | 1 year | 10/16 | 0.95 | 0.90 | 0.91 |
| 10 | 13 | 64 | 1 year | 9/13 | 1.13 | 0.36 | 0.35 |
| 11 | 15 | 72 | 4 years | 20/20 | 0.22 | 0.27 | 0.25 |
| 12 | 16 | 72 | 1.5 years | 10/15 | 0.19 | 0.22 | 0.20 |

TABLE 2-continued

Inhibiting effect of Ropren and changes of enzymatic activity of MAO in blood plasma of patients

| | | | | Parameters | | MAO activity (nmol of released ammonia per minute per mg of protein) | | |
|---|---|---|---|---|---|---|---|---|
| No | No. of patient's card | Age | History of disease | | Evaluation of mental status before and after treatment (points) | Before treatment | After 2 months | After treatment |
| 13 | 19 | 76 | 1 year | | 5/10 | 0.28 | 0.30 | 0.31 |
| 14 | 11 | 77 | 3 years | | 2/7 | 0.65 | 0.47 | 0.47 |
| 15 | 20 | 74 | 1 year | | 10/14 | 1.26 | 0.76 | 0.78 |

Before the treatment, the MAO activity of blood plasma in most of the patients was above the norm by 1.3-2.9 times, and only in 3 patients was it below the norm and remained at that level during the entire treatment period (Table 2). Ropren therapy resulted in the reduction of MAO activity in almost all patients to normal levels or to values close to normal. After comparison of the data on enzymatic activity and the therapeutic effect, it can be concluded that the best improvement of the general condition of the patients from this group occurred in 5 men (Record cards No. 4, 5, 7, 8 and 13). All of them had anxious-depressive and dementia syndromes. The general condition of the patients improved by the $2_{nd}$ month and remained at this level until the end of the trial and was accompanied by the reduction of anxious-depressive and hypochondriac syndromes. All these patients had a slight improvement of cognitive functions (by 3-4 points on average as per MMSE scale) and reported some "feelings of joy". Biochemical blood indices in this group of patients have a tendency to show a reduction of blood cholesterol and blood sugar.

The inhibiting effect was established in the other group of patients ($2^{nd}$ group) with weak or moderate form of dementia (age from 54 to 74) and a shorter history of the disease—from 6 months to 3 years. The developing dementia syndrome and changes in MAO activity in the blood plasma of these patients resulted from cranio-cerebral trauma, organic brain disorder, and chronic alcoholism (Table 3).

TABLE 3

Inhibiting effect of Ropren and changes of enzymatic activity of MAO in blood plasma in the $2^{nd}$ group of patients

| | | | Parameters | | MAO activity (nmol of released ammonia per minute per mg of protein) | | |
|---|---|---|---|---|---|---|---|
| No | Patient card No. | Age of patient | Duration of disorder | Evaluation of mental status before/after treatment (points) | Before treatment | After 2 months | After treatment |
| 1 | 9 | 63 | 1 year | 7/14 | 0.82 | 0.76 | 0.69 |
| 2 | 10 | 60 | 3 years | 3/7 | 0.78 | 0.62 | 0.61 |
| 3 | 14 | 74 | 1.5 years | 16/19 | 0.88 | 0.69 | 0.67 |
| 4 | 17 | 57 | 1 | 16/20 | 0.40 | — | 0.45 |
| 5 | 18 | 64 | 1 | 16/20 | 0.30 | — | 0.32 |
| 6 | 21 | 59 | 1 | 14/27 | 1.03 | 0.98 | 0.88 |
| 7 | 22 | 66 | 6 months | 21/28 | 0.85 | 0.81 | 0.66 |
| 8 | 23 | 56 | 6 months | 15/26 | 0.78 | 0.68 | 0.68 |
| 9 | 24 | 73 | 1 year | 15/26 | 0.77 | 0.79 | 0.75 |
| 10 | 25 | 54 | 1 year | 18/26 | 0.87 | 0.91 | 0.94 |

In 3 patients MAO activity in the blood serum remained unchanged, whereas in the rest of the patients the activity reduced as a result of Ropren treatment. Comparison of enzymatic activity of MAO in this group of the patients with the first group demonstrated that the Ropren therapy produced a significant therapeutic effect reflected in both the functional condition (EEG data and mental status (high average score as per the MMSE scale), and the biochemical blood indices. Data on changes of biochemical blood indices and EEG parameters in the $2^{nd}$ group of patients before and after treatment with Ropren are presented in Table 4.

TABLE 4

Changes in biochemical blood indices and EEG parameters in the 2$^{nd}$ group of patients after 3 months of treatment with Ropren

| Patient card No. Duration of disorder | Before treatment with Ropren After treatment with Ropren | Biochemical blood indices | | | | | Evaluation of mental status, (points) | EEG data Changes of EEG parameters |
|---|---|---|---|---|---|---|---|---|
| | | Cholesterol | AP | ALT | Sugar | Bilirubin | Thymol test | | |

| Patient / Duration | Treatment | Cholesterol | AP | ALT | Sugar | Bilirubin | Thymol test | Mental status (points) | EEG changes |
|---|---|---|---|---|---|---|---|---|---|
| 14 | Before treatment | 6.01 | 171.0 | 21.6 | 6.01 | 15.01 | 0.2 | 16 | Continuous |
| 1 year and 6 months | After treatment | 5.91 | 174.1 | 26.7 | 5.27 | 15.54 | 0.3 | 19 | α-rhythm |
| 9 | Before treatment | 4.72 | 169.4 | 47.2 | 6.81 | 19.27 | 0.5 | 7 | — |
| 1 year | After treatment | 4.81 | 167.8 | 42.4 | 6.87 | 18.27 | 0.4 | 14 | — |
| 10 | Before treatment | 6.82 | 169.7 | 36.4 | 6.07 | 17.23 | 0.4 | 3 | Continuous |
| 3 years | After treatment | 6.27 | 168.9 | 37.4 | 5.59 | 15.71 | 0.3 | 7 | |
| 17 | Before treatment | 6.01 | 169.1 | 32.7 | 4.27 | 15.27 | 0.3 | 16 | Continuous |
| 1 year | After treatment | 5.89 | 168.7 | 37.1 | 4.08 | 15.07 | 0.2 | 20 | Normal range |
| 18 | Before treatment | 4.78 | 161.0 | 37.1 | 4.89 | 15.01 | 0.1 | 12 | No changes |
| 1 year | After treatment | 4.89 | 159.8 | 37.4 | 4.81 | 15.54 | 0.3 | 17 | |
| 21 | Before treatment | 7.01 | 161.8 | 34.8 | 4.87 | 15.91 | 0.3 | 14 | Continuous |
| 1 year | After treatment | 6.68 | 161.3 | 40.4 | 5.11 | 17.61 | 0.4 | 27 | α-rhythm |
| 22 | Before treatment | 5.01 | 174.1 | 121.4 | 7.01 | 24.01 | 1.2 | 21 | Continuous |
| 6 months | After treatment | 5.71 | 168.1 | 37.2 | 6.41 | 15.61 | 0.3 | 28 | To norm |
| 23 | Before treatment | 4.85 | 151.4 | 74.2 | 7.01 | 21.04 | 1.0 | 15 | Continuous |
| 6 months | After treatment | 6.71 | 151.4 | 27.9 | 5.79 | 15.57 | 0.3 | 26 | |
| 24 | Before treatment | 5.71 | 161.4 | 97.6 | 7.07 | 41.2 | 2.0 | 10 | Continuous |
| 1 year | After treatment | 5.97 | 164.2 | 37.1 | 5.84 | 15.79 | 0.4 | 26 | α-rhythm |
| 25 | Before treatment | 6.07 | 148.4 | 71.0 | 5.81 | 21.04 | 1.4 | 18 | Continuous |
| 1 year | | 5.79 | 168.2 | 37.1 | 5.41 | 15.71 | 0.4 | 29 | α-rhythm |

Table 4 shows that in the patients from the 2$^{nd}$ group there was not only improvement of enzymatic activity of MAO to normal values, but also improvement of hepatic blood indices: reduction of levels of cholesterol, ALT, alkaline phosphatase, sugar, bilirubin, and thymol probe. According to EEG data, the general condition of the patients improved, with 8 out of 10 people having positive changes (80%). Use of Ropren resulted in appearance (or shifting) of α-rhythm, an increase of its amplitude and index, a reduction of accent in the left frontotemporal area. By the end of the treatment, there was complete reduction of depressive symptoms.

Therefore, Ropren has an inhibiting effect on MAO activity in the blood plasma. After 3-4 weeks of treatment, there was reduction of MAO activity by 1.5-3 times, that testifies to the functional improvement of the brain activity and improvement of the psychosomatic condition of the patients. In can be concluded, that Ropren therapy leads to improvement and normalisation of brain and liver functions as well as inhibition of MAO activity to the normal values.

The efficacy of the treatment with polyprenols of formula (1) of various psychiatric disorders with increased MAO activity in the blood was demonstrated in the examples cited below.

Example 1

Evaluation of the efficacy of Ropren on a group of patients with Alzheimer's type dementia, marked depression, memory loss, and increased MAO activity (25 people). The therapeutic substance was administered at the dose of 144 mg per day, 8 drops 3 times per day under the tongue. The efficacy of the treatment was evaluated based on changes in psychosomatic status using the following scales: questionnaire "list of symptoms", international hospital anxiety and depression scale HADS, and the MMSE scale reflecting the improvement of cognitive functions during the treatment.

By the 2nd month of the treatment with Ropren, there was a marked improvement in the general condition of the patients. There was disappearance of anxiety, complaints of depressive type, hypochondriacal complaints, tearfulness, and more rational behaviour was exhibited by the patients. Half of the patients noted the disappearance of headaches, dizziness and loss of coordination during walking Irritability and tendency to affective behaviour decreased. Evaluation of patients' wellbeing, based on questionnaire "list of symptoms", is presented in Table 5.

TABLE 5

Changes in psychosomatic state of patients suffering from chronic alcoholism in experimental and control groups before and after treatment with Ropren, assessed by questionnaire "list of symptoms"

| Parameters | Experimental group, 60 people | | Control group, 30 people | |
|---|---|---|---|---|
| | Before treatment | After treatment | Before treatment | After treatment |
| Age of patients | from 17 to 74 (average 56 ± 13) | | From 25-83 (average 62.83 ± 13.89) | |
| Males:Females | 47:13 | | 27:3 | |
| Duration of disorder (years) | From 3-20 | | From 3-20 | |
| Evaluation of severity of anxiety/depression in points using questionnaire "list of symptoms", in % | | | | |
| Absence of depression (norm 0-5 points) | | 75.0% (45 people) | | 37.9% (11 people) |
| Depression remains (6 points and more) | 100% (60 people) | 25% (15 people) | 100% (29 people) | 62.1% (18 people) |

The "list of symptoms" questionnaire indicates that as a result of the Ropren therapy, marked positive changes were found in relation to all of the above-cited symptoms.

The Table shows that Ropren had more a more marked effect on the relief of the anxiety-depressive and hypochondrial symptoms, than in the control group of patients who received basic therapy with antidepressants and cerebroprotectors.

The MMSE scale (parameter of evaluation of cognitive functions of a patient before and after treatment) was used for evaluation of the intellect. It is known that an increased level of MAO reduces the cognitive function of patients. Improvement of cognitive function was registered in 22 patients (88%) who received Ropren for at least 3 months. Differential diagnostics were conducted using encephalography (EEG) in 12 patients (48%) with dementia syndrome before and after treatment with Ropren. EEG analysis revealed positive changes in patients, according to data of both visual examination and analysis of power spectrums that comprise bioelectric activity (BEA). After treatment with Ropren, there was a distinct shift in spectral density towards a high-frequency range and alpha-rhythm, an increase of its activity, and a decrease of the emphasis in the left frontotemporal lobe. This indicates the optimisation of functional condition of cortical neurons, expressed through their activation in patients after the Ropren therapy (75%). After Ropren therapy, there were no changes in 2 patients (16.6%), and negative changes were registered in 1 patient.

TABLE 6

Characteristics of patients with dementia syndrome, including Alzheimer's type and Parkinson's syndrome, treated with Ropren

| Parameter | Before treatment | After treatment |
|---|---|---|
| Age | 66.76 | Same |
| Males:Females | 14:11 | Same |
| Duration of disorder | From 3 months to 3 years | Same |
| Evaluation of severity of dementia as per MMSE scale | % | % |
| Very light | None | 12 |
| Light | 12 | 32 |
| Moderate | 36 | 20 |
| Moderatly severe | 32 | 24 |
| Severe | 20 | 12 |

Example 2

Evaluation of therapeutic efficacy of Ropren in patients with increase level of MAO in the blood and suffering from chronic alcoholism and/or drug addiction and disorders related to the principal disease; Comparison of the efficacy of Ropren therapy with the commonly-used basic detoxicating therapy (60 people). The effect of Ropren on the risk of the development of complications after alcohol (alcohol surrogates) or drugs poisoning and mental and neurological status was evaluated before and after the treatment (Table 7).

TABLE 7

Characteristics of patients with $2^{nd}$ stage chronic alcoholism and drugs and nicotine addiction

| Parameters | Control group, 30 people | Experimental group, 60 people |
|---|---|---|
| Age of patients | 62.83 ± 13.89 | 56 ± 13.0 |
| Males:Females | 27:3 (9:1) | 47:13 (3.6:1) |
| Average duration of disease | 9.8 ± 1.97 | 9.9 ± 1.,69 |
| Duration of disease: | | |
| Up to 5 years (% of patients) | 36.7% | 31.7% |
| 6-10 years (% of patients) | 43.3% | 45.0% |
| over 10 years (% of patients) | 20% | 23.3% |
| patients with pneumonia | 23.3% | 11.7% |
| patients with hepatitis "B", "C" | 30.0% | 33.3% |
| patients taking drugs (heroin, opium) | 3.3% | 13.3% |
| HIV-infected patients | 3.3% | 11.7% |
| patients with type 2 diabetes | 13.3% | 5% |
| patients with convulsive disorder | 10.0% | 20% |
| patients with acute alcohol syndrome | 3.3% | 5% |
| patients with acute alcohol induced suicidal state | 3.3% | 5% |
| patients with coronary heart disease and type 2 hypertension | 23.3% | 5% |
| patients with toxicomania and poisoning | — | 6.7% |
| people with oncological symptoms | — | 1.7% |
| patients with cranio-cerebral trauma | — | 3.3% |
| patients with Korsakov's amnestic syndrome | — | 3.3% |
| patients with secondary syphilis | — | 3.3% |
| patients with schizophrenia | — | 5% |
| patients with obesity of 3-$4^{th}$ degree | — | 3.3% |
| patients with tick-borne encephalitis | — | 1.7% |
| patients with nicotine addiction | 75% | 80% |

Evaluation was based on a method of neurological and psychiatric examination of the patients using screening scales ("list of symptoms" questionnaire, HADS scale of anxiety/depression, and Young's scale of neurotic disorders). The patients were examined using a clinical psychiatric method by conducting a semi-structured interview, (Methods for evaluation of emotional status HADS scale, (Zigmond A. S. and Snaith R. P., 1983)) before and after the treatment. For interpretation of data using this scale, a summary index of each subscale (A—anxiety, D—depression) is considered. It is divided into 3 grades of values:—0-7 points—"normal"; 8-10 points—"subclinical anxiety/depression"; 11 points and above—"clinical anxiety/depression". Evaluation of somatic-vegetative status using a "list of symptoms" questionnaire was conducted before and after treatment.

Evaluation of Ropren's effect on brain function was based on changes in encephalography (EEG) (Table 8). Electronic EEG data processing allowed for detecting changes in rhythms in the presence of epiactivity in the brain, since EEG epicomplexes are often registered in patients suffering from alcoholism. As a result of the Ropren treatment, it was established that 66% of the patients had the distinct positive changes on EEG, whereas in the control group this effect was found only in 23.5% of the patients, with 76.5% having no significant changes after the basic therapy. In the control group of patients, negative changes were registered on average 10-11 times more often than in the group administered the substance of formula (1).

TABLE 8

Comparative analysis (% of patients) of experimental and control groups of patients with addiction to psychoactive substances, according to EEG data after treatment

| Changes | Experimental group of patients treated with Ropren | Control group of patients that received basic therapy |
|---|---|---|
| Negative changes | 2% | 23.5% |
| Without significant changes | 14% | 35% |
| Unclear changes | 18% | 18% |
| Total: | 34% | 76.5% |
| Insignificant positive changes | 24% | 23.5% |
| Positive changes | 11% | — |
| Expressed positive changes | 31% | — |
| Total: | 66% | 23.5% |

The effect of Ropren was assessed in patients with syndromes that accompany alcoholism related disorders: polyneuritis of extremities before and after treatment (on Young's scale), focal cerebral symptoms, and changes in cases of epileptic fits and Parkinson's syndrome. Diagnostics of the patients were conducted by a psychiatrist, neurologist and a specialist in functional diagnostics by screening scales, which allow for assessing the severity of a disease and the degree of development of a process, as well as for evaluation of the efficacy of the new therapeutic substance used in patients with $2^{nd}$ degree chronic alcoholism and drug addiction.

As a result of Ropren treatment, using the same doses as in Example 1, there were distinct positive changes in relation to psychosomatic and neurological disorders. Particularly marked improvement (subjective and objective) of the general condition of the patients was found in relation to psychosomatic disorders: disappearance of anxiety, depressive type complaints, hypochondriacal complaints, and tearfulness. Disturbing feelings of internal pressure, anxiety and unpleasant somatic feelings disappeared. A marked improvement in mood (with some showing an undertone of euphoria) was registered in 90% of the cases. In 80% of the patients, disappearance of headaches, dizziness, loss of coordination during walking, numbness of limbs, and body tremor was noted. In six patients with anxiety-depressive symptoms, the psychotic symptoms (alcohol hallucinations, paranoia) were fully relieved without the use of antidepressants, which were administered to the control group. Based on the hospital scale HADS, the improvement after treatment with Ropren was as follows:

without signs of depression ("normal")—in 80.0% of patients;
depression remains in "subclinical form"—in 16.7% of patients;
depression remains in "clinical form"—in 3.3% of patients.

Neurological disorders (PNP) transformed from a severe and moderately-severe form into a weak form; 10% of the patients with polyneuritis of limbs in the experimental group fully recovered.

In the control group of patients on the 30th day after the basic therapy (B group vitamins, nootropics, and cerebroprotectors), 29 patients showed improvement in mental state, with marked improvement (based on "list of symptoms" questionnaire) found in 37.9% of the patients, whereas in 62.1% the symptoms of depression persevered.

Positive changes in the psychosomatic state of the patients were found in only 55.2% as per the HADS scale, whereas depression remained in 44.8%, i.e. subclinical and clinical anxiety-depressive symptoms remained in 10 out of 29 patients. Neurological disorders (polyneuropathy) persevered in 86.2% of the patients from the control group, with none of them fully recovering after the treatment.

Therefore, Ropren showed efficacy in the treatment of alcohol abstinence syndrome on the background of chronic alcoholism and/or drug addiction. This was shown in the form of a reduction of depression, abstinence syndrome and related neurological and psychiatric symptoms.

Examples of the distinct positive effect of Ropren in treatment of various psychiatric disorders are cited below.

Patient N. Acute alcoholic hallucinations, $2^{nd}$ degree chronic alcoholism, suicidal attempts. 28 y.o., duration of the disease—7 years. Level of MAO before the treatment was 1.09 nmol ammonia/min/mg of protein and after the treatment was 0.48 nmol ammonia/min/mg of protein. Anamnesis: suicidal attempt in a drunken state (poisoning by phenazepam); concomitant disease: chronic viral hepatitis C. Diagnosis of a neurologist: toxic encephalopolyneuropathy with epileptic symptoms. The patient had complaints on having fever, shaking, headaches, a feeling of coldness in the hands and feet. As a result of the treatment, alcohol abstinence syndrome was relieved on the $6^{th}$ day. The patient put on 3 kg of body weight. Biochemical blood indices improved on the $15^{th}$ day after commencement of treatment with Ropren, by the $30^{th}$ day, they had returned to normal levels. An improvement in mental state took place by the end of the treatment: from 56 to 0 points as per the "list of symptoms" questionnaire, from 32 to 4 points as per HADS scale, testifying to the absence of signs of depression. On the $30^{th}$ day, the condition of the patient improved significantly with a gradual reduction of dysarthria, coordination disorders, and vibrational sensitivity, and a decrease in polyneuropathic loss of reflexes (transformation from the marked form of PNP into moderate form). EEG data revealed marked positive changes in the form of normalisation of BEA: significant increase in alpha activity and reduction of irritative manifestations. Before treatment, the alpha-rhythm was significantly reduced both in index and amplitude (short segments of 8 Hz and 10 mcV in the occipital area), there was domination of low-amplitude polymorphic slow activity. After the treatment, the initial moderate diffusive changes of BEA approached the permissible normal values.

This example demonstrated the efficacy of Ropren in treatment of patients with chronic alcoholism with an increased level of blood cholesterol, and suicidal poisoning attempts when in a drunken state. Therefore, detoxicating treatment with Ropren of chronic alcoholism with suicidal syndrome revealed the evident improvement of patients' conditions. In these patients, abstinence syndrome was arrested relatively quickly on the $3^{rd}$-$6^{th}$ day after commencement of treatment.

Patient H. Schizophrenia complicated by alcoholism. Patient's card No. 7; 40 y.o.; duration of the disease—7 years. Alcohol abstinence syndrome, $2^{nd}$ degree chronic alcoholism, toxic encephalopolyneuropathy. Level of MAO before treatment—0.63-0.43 nmol of ammonia/min/mg of protein. Diagnosis based on EEG: schizophrenia complicated by $2^{nd}$ degree chronic alcoholism. Alcohol abstinence syndrome was relieved on the $17^{th}$ day after commencement of treatment. By the end of the treatment, there were distinct positive changes in the form of significant intensification of alpha-rhythm. These changes testify the normalisation of functional condition of the cortex and the reduction of irritative manifestations. At the beginning of the treatment, polyneuropathic loss of reflexes was moderate (4 points as per Young's scale), and by the end of the treatment it had normalised (0 points). For neurological status, there was a complete regression of focal symptoms and polyneuropathic loss of reflexes. After treatment, depression disappeared. There were improvements in the functional condition of the CNS.

Patient C. Chronic alcoholism, drug addiction, 35 y.o., duration of the disease–12 years. Drugs of the opium group had been used for more than 17 years, and methadone (i/v)—for more than the last 7 years. Diagnosis: chronic alcoholism, drug addiction (heroin). Main syndrome: abstinence+depressive syndrome. The compound of formula (1) was prescribed 3 times daily before food for a period of 1 month together with basic therapy. Recovery of abstinence syndrome was registered on the $3^{rd}$ day. According to an examination of a neurologist, complete regression of focal symptoms and polyneurotic disorders occurred by the $30^{th}$ day. Almost all biochemical parameters of the blood normalised on 15th day.

The data obtained allow us to conclude that the use of Ropren in patients with chronic alcoholism using the suggested methodology provides the normalisation of psychosomatic states and recovery from depression.

As a result of the treatment, biochemical blood indices normalised in the experimental group by the $15^{th}$ day: levels of AP, ALT, AST, MAO, bilirubin, urea, creatinine, amylase and blood sugar. This process was less evident in the control group of patients.

Polyprenols of formula (1) can be administered to patients on its own or in combination with other pharmaceuticals.

Examples of pharmaceutical compositions such as solution, suspension, capsules, or the liposomal form are cited below.

Liquid Oral Form of the Substance.

It contains the following components, weight %

| Substance of formula (1) | 10-60 |
|---|---|
| Sunflower oil | the remainder |

Below is one of the possible examples of liquid therapeutic form:

Example 1

| Substance of formula (1) | 25 ± 0.5 |
|---|---|
| Sunflower oil | the remainder |

To obtain the therapeutic form, the substance of formula (1) and sunflower oil are mixed at the given ratio, packed into flasks using a doser, and sterilised.

Example 2

Suspension for parenteral administration. It contains the following components, weight %

| The compound of formula (1) | 20.0 |
|---|---|
| Tween 80 | 25.0 |
| Ethanol | 4.0 |
| Polypropylene glycol | 10.0 |
| Pyrogen free water | the remainder |

To obtain this therapeutic form the substance of formula (1) is mixed with ethanol, polypropylene glycol, Tween 80 and heated water and thoroughly stirred; the mixture is dispensed into ampoules and sterilised.

Example 3

Gelatine capsules. Capsules contain the following components, weight %

| The compound of formula (1) | 46.0 |
|---|---|
| Copolymer of methacrylic acid | 12.0 |
| Talc | 5.7 |
| Copolymer of methacrylic and acrylic acids | 18.0 |
| Glycerol triacetate | 3.3 |
| Magnesium stearate | 15.0 |

Example 4

Gelatine Capsules

| Weight of capsules | 238-262 mg (100%) |
|---|---|
| The substance of formula (1) | 20 weight % of capsule's weight |

Example 5

Gelatine Capsules

| Weight of capsules | 240-260 mg (100%) |
|---|---|
| The substance of formula (1) | 6 weight % of capsule's weight |
| Sunflower oil | 14 weight % of capsule's weight |

Example 6

Gelatine Capsules

| Weight of capsules | 240-260 mg (100%) |
|---|---|
| The substance of formula (1) | 4 weight % of capsule's weight |
| Soy oil | 16 weight % of capsule's weight |

Example 7

Gelatine Capsules

| Weight of capsules | 412-420 mg (100%) |
|---|---|
| Substance of formula (1) | 48 ± 0.5 weight % of capsule's weight |

Example 8

Gelatine Capsules

| Weight of capsules | 412-420 mg (100%) |
|---|---|
| Substance of formula (1) | 2.4 ± 0.1 weight % of capsule's weight |
| Sunflower oil | 47 ± 0.2 weight % of capsule's weight |
| Sodium ascorbate | 0.1 weight % of capsule's weight |
| Vitamin $B_6 + B_{12}$ | 0.1 weight % of capsule's weight |

Example 9

Gelatine Capsules

| | |
|---|---|
| Weight of capsules | 412-420 mg (100%) |
| Substance of formula (1) | 10 ± 0.2 weight % of capsule's weight |
| Sodium ascorbate | 0.1% of capsule's weight |
| Vitamin $B_6 + B_{12}$ | 0.1% of capsule's weight |

Example 10

Gelatine Capsules

| | |
|---|---|
| Weight of capsules | 208-212 mg (100%) |
| Substance of formula (1) | 24 ± 0.2 weight % of capsule's weight |

Example 11

Gelatine Capsules

| | |
|---|---|
| Weight of capsules | 208-212 mg (100%) |
| Substance of formula (1) | 5 ± 0.1 weight % of capsule's weight |
| Sunflower oil | 19 ± 0.2 weight % of capsule's weight |

Capsules described in Examples 3-11 do not contain any components of animal origin. To obtain the therapeutic substance, the substance of formula (1) is mixed with vegetable oil(s), and any other excipients present, at the given ratios and fed into an apparatus that prepares the therapeutic form. Capsules are dried to a water content of 3-5% at a temperature of not more than 45° C.

Example 12

Liquid Liposomal Form of the Substance
It contains the following components, weight %

| | |
|---|---|
| The compound of formula (1) | 0.4 |
| Lecithine | 4.0 |
| Preservative | 0.001-0.2 |
| Water | the remainder |

The liposomal form was prepared using the method of mechanical emulsification of the liquid phase from soy-bean lecithin, which was subjected to additional purification. The substance of formula (1) was added to a composition of lipids in chloroform solution with further evaporation and subsequent addition of water and emulsification.

INDUSTRIAL APPLICATIONS

Therefore, results of the clinical trials of the therapeutic substance based on polyprenols of formula (1), allow one to make a conclusion about the efficacy of the treatment of patients with excessive activity of monoamine oxidase and symptoms of mental disorders (Alzheimer's, Parkinson's, and Huntington's diseases); and/or progressive reduction of cognitive functions related to the above-mentioned diseases; and/or dependence on psychoactive substances, nicotine, and ethanol; and/or symptoms of withdrawal from psychoactive substances, nicotine, and ethanol in combination with suicidal attempts.

Due of the absence of side effects, treatment with polyprenols of formula (1) can continue for an extended period of time. Ropren is inexpensive substance, the production of which is based on an established method for extraction from green verdure of conifers.

The invention claimed is:

1. A method of treating excessive monoamine oxidase activity in a human patient in need thereof, said method comprising administering a therapeutically effective amount of a composition comprising a polyprenol of formula (1)

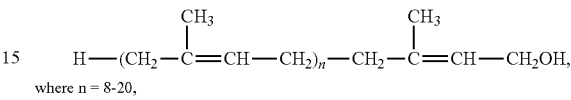

where n = 8-20, wherein said therapeutically effective amount provides a total daily dose of said polyprenol of 1-150 mg per day.

2. A method of inhibiting monoamine oxidase activity in a human patient in need thereof, said method comprising administering a therapeutically effective amount of a composition comprising a polyprenol composition of formula (1)

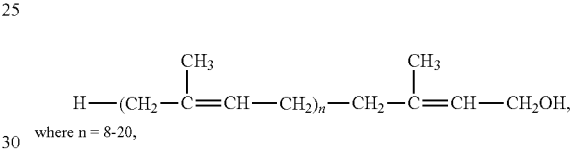

where n = 8-20, wherein said therapeutically effective amount provides a total daily dose of said polyprenol of 1-150 mg per day.

3. The method according to claim 1 or 2 wherein n=10-16.

4. The method according to claim 1 or 2 wherein said composition further comprises one or more pharmaceutically acceptable excipients, carriers, solvents, additives and/or lubricants.

5. The method according to claim 4 wherein said composition is prepared in the form of a solution, suspension, coated tablet, capsule, rectal suppository or in liposomal form.

6. The method according to claim 5 wherein said composition is an oil solution, a suspension for parenteral administration or a solid form for oral administration and wherein the polyprenol constitutes from 0.10 to 80 weight % of the composition.

7. The method according to claim 1 or 2 wherein the method comprises administering said therapeutically effective amount in one dose per day.

8. The method according to claim 1 or 2 wherein the method comprises administering said therapeutically effective in more than one dose per day.

9. The method according to claim 1 or 2 wherein the patient is not suffering from dementia syndrome.

10. The method according to claim 1 or 2 wherein the method is effected over a period of time of at least 3 months.

11. The method according to claim 10 wherein the method results in a reemergence of or improvement in EEG alpha-rhythms.

12. The method according to claim 10 wherein the method results in a reduction in one or more biochemical blood indices selected from the group consisting of cholesterol, alkaline phosphatase (AP), alanine-amino transferase (ALT), sugar, bilirubin and thymol test.

* * * * *